US009095730B2

(12) United States Patent
Angel et al.

(10) Patent No.: US 9,095,730 B2
(45) Date of Patent: Aug. 4, 2015

(54) ASSOCIATIVE THICKENERS BASED ON METHACRYLATE

(75) Inventors: Maximilian Angel, Schifferstadt (DE); Peter Hossel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 485 days.

(21) Appl. No.: 13/490,615

(22) Filed: Jun. 7, 2012

(65) Prior Publication Data

US 2012/0315237 A1 Dec. 13, 2012

Related U.S. Application Data

(60) Provisional application No. 61/493,986, filed on Jun. 7, 2011.

(51) Int. Cl.

| *A61Q 5/10* | (2006.01) |
| *A61Q 5/06* | (2006.01) |
| *A61K 47/32* | (2006.01) |
| *A61K 8/81* | (2006.01) |
| *C08F 2/00* | (2006.01) |
| *A61Q 5/02* | (2006.01) |
| *A61Q 5/12* | (2006.01) |
| *A61Q 5/00* | (2006.01) |

(52) U.S. Cl.
CPC .............. *A61Q 5/06* (2013.01); *A61K 8/8152* (2013.01); *A61K 8/8158* (2013.01); *A61K 47/32* (2013.01); *C08F 2/00* (2013.01); *A61K 2800/48* (2013.01); *A61Q 5/006* (2013.01); *A61Q 5/02* (2013.01); *A61Q 5/10* (2013.01); *A61Q 5/12* (2013.01)

(58) Field of Classification Search
None
See application file for complete search history.

(56) References Cited

U.S. PATENT DOCUMENTS

| 4,380,600 | A |   | 4/1983 | Hosoda et al. |
| 4,769,167 | A |   | 9/1988 | Haas et al. |
| 5,290,869 | A | * | 3/1994 | Kinoshita et al. ............. 525/291 |
| 5,705,553 | A | * | 1/1998 | Kuropka ....................... 524/459 |
| 5,936,026 | A |   | 8/1999 | Huybrechts et al. |
| 6,503,975 | B1 | * | 1/2003 | Huybrechts ................... 524/501 |
| 8,232,356 | B2 |   | 7/2012 | Leyrer et al. |
| 2006/0228317 | A1 |   | 10/2006 | Chrisstoffels et al. |
| 2008/0194715 | A1 |   | 8/2008 | Wendel et al. |
| 2008/0199416 | A1 |   | 8/2008 | Nguyen-Kim et al. |

FOREIGN PATENT DOCUMENTS

| DE | 2050248 | 5/1971 |
| DE | 2924663 | 12/1979 |
| DE | 3404537 | 8/1985 |
| DE | 3818868 | 12/1989 |
| DE | 4318033 | 12/1994 |
| DE | 19710215 | 9/1998 |
| DE | 10048888 | 4/2002 |
| DE | 10311616 | 9/2004 |
| EP | 11806 | 6/1980 |
| EP | 0549280 | 6/1993 |
| EP | 761780 | 3/1997 |
| WO | WO-2006/106114 | 10/2006 |
| WO | WO-2006/106140 | 10/2006 |
| WO | WO-2007/010035 | 1/2007 |
| WO | WO-2007/017434 | 2/2007 |
| WO | WO-2007/024457 | 3/2007 |
| WO | WO-2009/062994 | 5/2009 |
| WO | WO 2009138493 A1 * | 11/2009 ............... C08F 2/38 |

OTHER PUBLICATIONS

"Machine Translation of DE4318033", 9 pages.
Rauch-Puntigam, Harald et al., "Acryl-und Methacrylverbindungen", *Chemie, Physik und Technologie der Kunststoffe in Einzeldarstellungen* 1967 , 2 pages.
Umbach, Wilfried , "Kosmetik und Hygiene von Kopf bis Fuss (Cosmetics and Hygiene from Head to Toe)", *3rd Edition, Wiley-VCH*, 2004 , pp. 123-128.
Umbach, Wilfried , "Kosmetik und Hygiene von Kopf bis Fuss (Cosmetics and Hygiene from Head to Toe)", *3rd Editiion, Wiley-VCH*, 2004 , pp. 235-236.
PCT International Preliminary Report on Patentability in PCT/EP2012/058419, dated Dec. 10, 2013, 6 pages.
PCT International Search Report in PCT/EP2012/058419, mailed Jul. 2, 2012, 2 pages.
PCT International Written Opinion in PCT/EP2012/058419, mailed Jul. 2, 2012, 5 pages.

* cited by examiner

*Primary Examiner* — Mark Kaucher
(74) *Attorney, Agent, or Firm* — Servilla Whitney LLC

(57) ABSTRACT

Provided is a process for the preparation of methacrylate-based polymers soluble in aqueous medium, which can be used, in particular, as associative and non-associative thickeners.

6 Claims, No Drawings

ASSOCIATIVE THICKENERS BASED ON METHACRYLATE

CROSS-REFERENCE TO RELATED APPLICATIONS

This application claims the benefit of priority of U.S. Provisional Application No. 61/493,986, filed on Jun. 7, 2011, the entire content of which is hereby incorporated by reference in its entirety.

TECHNICAL FIELD

The invention relates to an improved process for the preparation of methacrylate-based polymers soluble in aqueous medium, which can be used, in particular, as associative and non-associative thickeners.

BACKGROUND

Thickeners serve to increase the viscosity of flowable compositions.

Thickeners that are customary, in particular, in cosmetics are, for example, high molecular weight polyacrylic acids (INCI name: Carbomer), which are used in their neutralized form as water-soluble thickeners.

Associative thickeners is the term used to refer to polymers which, although they are rendered water-soluble with ionic groups such as carboxyl groups, have a thickening effect which is not based on their high molecular weight, but on the fact that the longchain aliphatic side groups incorporated in small amounts into the polymers associate.

These polymers can be prepared, for example, as solution polymers or emulsion polymers and be used starting from this form. Polymers of this type are described, for example, in DE 3404537 and EP 11806 (Dow Chemicals).

Although most of the polymers known as thickeners have very good thickening properties, they also have disadvantages, when further requirements are placed on them apart from the thickening effect.

It is often desired, particularly in cosmetics, that polymers simultaneously satisfy a plurality of tasks, for example in addition to the thickening property, also have film forming properties.

The film-formation in hair cosmetics serves primarily to set the hair or to be able to better shape it.

Although known emulsion polymers, which are often based on ethyl acrylate, are good film formers, they are often too sticky and therefore also do not have satisfactory setting properties. The films formed by them are too soft and do not impart any additional performance to the hair.

SUMMARY

Embodiments of the present invention are directed to a process for the preparation of polymers P, the process comprising polymerizing at least one polymer A and at least one polymer B, wherein (A) polymer A comprises, in polymerized-in form: a1) 30 to 70% by weight of $C_1$-$C_4$-alkyl(meth)acrylate, a2) 30 to 70% by weight of (meth)acrylic acid, a3) 0 to 20% by weight of monomers substituted with a $C_8$-$C_{30}$-radical, and a4) 0 to 20% by weight of further monomers different from a1) to a3), provided that the amounts of a1) to a4) add up to 100% by weight; and (B) polymer B comprises, in polymerized-in form: b1) at least one monomer b1) which carries at least one amide group, and b2) optionally further monomers b2) different from b1); wherein one of the polymers A or B is prepared in the presence of the other polymer in each case.

In one or more embodiments, the preparation of the polymer A or B is only started when more than 99% by weight of the amount of all monomers to be used for the preparation of the other polymer in each case have been polymerized.

In one or more embodiments, the polymerization of the monomers b1) and b2) is only started when more than 99% by weight of the amount of all monomers a1) to a4) to be used for the preparation of polymer A have been polymerized.

In one or more embodiments, the preparation of polymer A or B is started when in the region of from 50 to 99% by weight of all monomers to be used for the preparation of the other polymer in each case have been polymerized.

In one or more embodiments, the preparation of polymer A or B is started when in the region of from 10 to 50% by weight of all monomers to be used for the preparation of the other polymer in each case have been polymerized and is ended before more than 80% of the amount of all monomers to be used for the preparation of the other polymer have been polymerized.

In one or more embodiments, the preparation of the polymers A to B takes place by radical emulsion polymerization.

In one or more embodiments, the polymer P comprises polymers A and B in a weight ration A:B in the range from 50:50 to 98:2.

In a specific embodiment, the at least one monomer b1) is methacrylamide. In a specific embodiment, a1) comprises ethyl acrylate and a2) comprises methacrylic acid.

A second aspect of the present invention is directed to a polymer P obtainable by the process according to the invention.

A further aspect of the present invention is directed to a cosmetic preparation comprising the polymer P according to the invention.

A still further aspect of the present invention is directed to a method of thickening a cosmetic preparation, the method comprising using the polymer P according to the invention as a thickener.

A yet further aspect of the present invention is directed to a method of treating hair, the method comprising bringing the hair into contact with the polymer P according to the invention.

DETAILED DESCRIPTION

The present invention provides polymeric associative and nonassociative thickeners which, apart from their thickening effect, offer an advantageous application as film former starting from the aqueous medium and, as far as possible, further advantages when used in cosmetic applications.

Gel-like preparations for cosmetics should combine as many of the following properties as possible:
  the resulting gels should be as clear as possible,
  the resulting gels should be able to be distributed easily in the hair and give it good hold, which can be achieved particularly readily by gels with thixotropic properties,
  the resulting gels should themselves have film-forming properties and thus contribute to the setting of the hair,
  the resulting gels should have conditioning properties and improve the sensory properties of the hair, e.g. give it suppleness and shine and, after drying be non-sticky or only slightly sticky, the hair treated with the resulting gels should have good
    wet combability (thus, the freshly treated hair can be
    easily shaped using the comb in order to form the desired
    hairstyle),
the polymers used for the preparation of the gel should
    make it possible for gels to be able to be formulated in as
    many cosmetically acceptable pH ranges as possible,
    specifically in the pH range from about 5 to 9,
the polymers used for the preparation of the gel should
    permit the formulation of gels whose properties are switchable via the pH,
the polymers used for the preparation of the gel should be
    able to be formulated together with standard commercial
    thickeners.

The present invention provides a process for the preparation of polymers P, the process comprising polymerizing at least one polymer A and at least one polymer B, wherein
(A) polymer A comprises, in polymerized-in form:
    a1) 30 to 70% by weight of $C_1$-$C_4$-alkyl(meth)acrylate,
    a2) 30 to 70% by weight of (meth)acrylic acid,
    a3) 0 to 20% by weight of $C_8$-$C_{30}$-alkyl-substituted monomers, and
    a4) 0 to 20% by weight of further monomers different from a1) to a3),
    provided that the amounts of a1) to a4) add up to 100% by weight; and
(B) polymer B comprises, in polymerized-in form:
    b1) at least one monomer b1) which carries at least one amide group, and
    b2) optionally further monomers b2) different from b1);
    wherein one of the polymers A or B is prepared in the presence of the other polymer in each case.

"Preparation of polymer A" or "preparation of polymer B" is understood as meaning the polymerization of the monomers a1) to a4) or b1) and b2), respectively.

The prior art discloses numerous polymers which are prepared by polymerization in the presence of polyvinylpyrrolidone (PVP). Examples to be mentioned here are DE 3818868 (polystyrene in PVP), DE 19710215 (polyvinylformamide in PVP), DE 2050248 (vinyl chloride-vinyl ether copolymers in PVP), DE 10048888 (polyvinyl acetate in PVP), DE 10311616 (polyvinylformamide-g-PVP).

DE 2924663 describes a process for the preparation of aqueous dispersions of water-soluble polymer masses. Here, water-soluble monomers such as, for example, acrylic acid, acrylamide or dimethylaminoethyl methacrylate are polymerized in the presence of polymers such as polyethers, polyvinylpyrrolidone or polyvinyl acetate.

Polymer A a1) $C_1$-$C_4$-alkyl(meth)acrylate

Polymer A comprises, in polymerized-in form, 30 to 70% by weight, preferably 40 to 60% by weight, particularly preferably 45 to 55% by weight, of $C_1$-$C_4$-alkyl(meth)acrylate.

The $C_1$-$C_4$-alkyl(meth)acrylate a1) is preferably selected from methyl(meth)acrylate, ethyl(meth)acrylate, n-propyl(meth)acrylate, isopropyl(meth)acrylate, n-butyl(meth)acrylate, isobutyl(meth)acrylate, sec-butyl(meth)acrylate, tert-butyl(meth)acrylate and any desired mixtures thereof.

In one or more embodiments, a1) consists to at least 50% by weight, in a specific embodiment at least 80% by weight and in a very specific embodiment to at least 90% by weight, of ethyl acrylate. In an embodiment of the invention, a1) is or comprises ethyl acrylate.

The monomers a1) are polymerized into the polymers A) prepared according to the invention in an amount in the range from 30-70% by weight, preferably in the range from 40-60% by weight, based on the total amount of all monomers polymerized into the polymers A).

a2) (Meth)acrylic Acid

Polymer A comprises, in polymerized-in form, 30 to 70% by weight, preferably 35 to 59% by weight, particularly preferably 40 to 54% by weight, of (meth)acrylic acid.

The term "(meth)acrylic acid" comprises in the present case acrylic acid, methacrylic acid, and mixtures thereof. The term "(meth)acrylic acid" comprises here in each case both the neutral and also the neutralized, anionic form of (meth) acrylic acid.

In one or more embodiments, a2) consists of at least 50% by weight, in a specific embodiment of at least 80% by weight and in a very specific embodiment of at least 90% by weight, of methacrylic acid.

In an embodiment of the invention, a2) is or comprises methacrylic acid.

The monomers a2) are polymerized into the polymers A) prepared according to the invention in an amount in the range from 30-70% by weight, preferably in the range from 40-60% by weight, based on the total amount of all monomers polymerized into the polymers A).

a3) $C_8$-$C_{30}$-alkyl-substituted Monomers

Polymer A comprises, in polymerized-in form, 0 to 20% by weight, preferably 0.1 to 10% by weight, particularly preferably 0.5 to 7.5% by weight, of $C_8$-$C_{30}$-alkyl-substituted monomers.

The $C_8$-$C_{30}$-alkyl-substituted monomers a3) are preferably selected from monomers of the general formulae a3.1) and a3.2)

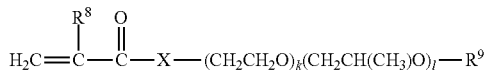

where
k and l, independently of one another, are integers in the range from 0 to 1000 and the sum k+l is at least 5,
$R^8$ is hydrogen or $C_1$-$C_4$-alkyl, preferably methyl,
$R^9$ is $C_8$-$C_{30}$-alkyl, $C_8$-$C_{30}$-alkenyl or $C_8$-$C_{30}$-alkylaryl, and
X is O or $NR^{10}$, where $R^{10}$ is selected from H, alkyl, alkenyl, cycloalkyl, heterocycloalkyl, aryl or hetaryl.

In one embodiment of the invention, the monomers c) are selected from $C_8$-$C_{30}$-alkyl-substituted monomers.

Connected directly to X in a3.1) or onto O in a3.2) is either at least one ethylene oxide radical (EO) or at least one propylene oxide radical (PO). In one or more embodiments, at least one EO is connected directly to X and O.

In an embodiment of the invention, the monomers a3.1) are esters of (meth)acrylic acid, thus $R^8$ in formula (a3.1) is H or preferably $CH_3$, with alkoxylated alcohols.

Suitable alkoxylated alcohols are, for example, the alkoxylated
    linear alcohols from natural sources or from the Ziegler build-up reaction of ethylene in the presence of aluminum alkyl catalysts. Examples of suitable linear alcohols are linear $C_8$-$C_{30}$-alcohols, in particular $C_{12}$-$C_{30}$-alcohols. Particularly preferred alcohols which may be mentioned are: n-dodecanol, n-tetradecanol, n-hexadecanol, noctadecanol, n-eicosanol, n-docosanol, n-tetracosanol, n-hexacosanol, n-octacosanol, and/or n-triacontanol, and also mixtures of the aforementioned alcohols, for example NAFOL® grades such as NAFOL® 22+(Sasol).

Oxo alcohols such as, for example, isooctanol, isononanol, isodecanol, isoundecanol, isotridecanol (for example Exxal® grades 7, 8, 9, 10, 11, 13).

Alcohols which are branched in the 2 position; these are the Guerbet alcohols known to the person skilled in the art which are accessible by dimerization of primary alcohols via the so-called Guerbet reaction. Particularly preferred alcohols which may be mentioned here are: Isofol®12 (Sasol), Rilanit®G16 (Cognis).

Alcohols which are obtained by the Friedel-Crafts alkylation with oligomerized olefins and which then comprise an aromatic ring as well as a saturated hydrocarbon radical. Particularly preferred alcohols which may be mentioned here are: isooctylphenol and isononylphenol.

Alcohols of the general formula (4) of EP 761780 A2., p. 4

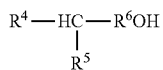

or alcohols of the general formula (5) of EP 761780 A2., p. 4

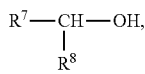

where $R^4$, $R^5$, $R^7$ and $R^8$, independently of one another, have the meaning described in EP 761780 A2., p. 4, lines 45 to 58; preferably, $R^4$, $R^5$, $R^7$ and $R^8$, independently of one another, are alkyl radicals having at least 4 carbon atoms and the total number of carbon atoms in the alcohols is at most 30, $R^6$ is an alkylene radical such as, for example, —$CH_2$—, —$CH_2$—$CH_2$—, —$CH_2$—$CH(CH_3)$—; For example, mention may be made here of 2-decyl-1-tetradecanol as suitable alcohol.

In one or more embodiments, at least one a3) is a (meth) acrylic acid ester of a mixture of ethoxylated $C_8$-$C_{30}$-, preferably $C_{12}$-$C_{30}$-, in particular $C_{16}$-$C_{22}$-fatty alcohols. In one embodiment, at least one a3) is a (meth)acrylic acid ester of a mixture of ethoxylated $C_8$-$C_{30}$-, preferably $C_{12}$-$C_{30}$-, in particular $C_{16}$-$C_{22}$-fatty alcohols, where the ethoxylated alcohols in each case comprise 20 to 30 EO radicals.

In one or more embodiments, at least one a3) is a (meth) acrylic acid ester of a mixture of ethoxylated $C_{12}$-$C_{18}$-fatty alcohols, where the ethoxylated alcohols in each case comprise 10 to 30 EO radicals.

In one or more embodiments of the invention, a3) is or comprises a methacrylic acid ester of a $C_{16}$-$C_{18}$-fatty alcohol ethoxylated with 25 mol of ethylene oxide (also referred to as "$C_{16-18}$-alkyl-PEG1100 methacrylates").

Such $C_{16-18}$-alkyl-PEG1100 methacrylates are commercially available for example as Plex®6877-0 (25% strength by weight preparation in methyl methacrylate) or Lutencryl®250 (50% strength by weight solution in methacrylic acid) or in VISIOMER® C18 PEG 1105 MA.

Further suitable monomers a3) are compounds of the general formula a3.1), where $R^8$ is H or preferably methyl, X is O, k and l are simultaneously zero and $R^9$ is $C_8$-$C_{20}$-alkylaryl or preferably $C_8$-$C_{20}$-alkyl.

Examples of such monomers a3) are n-octyl(meth)acrylate, 1,1,3,3-tetramethylbutyl(meth)acrylate, 2-ethylhexyl(meth)acrylate, n-nonyl(meth)acrylate, n-decyl(meth)acrylate, isodecyl(meth)acrylate, n-undecyl(meth)acrylate, isoundecyl(meth)acrylate, dodecyl(meth)acrylate, tridecyl(meth)acrylate, myristyl(meth)acrylate, pentadecyl(meth)acrylate, palmityl(meth)acrylate, heptadecyl(meth)acrylate, stearyl(meth)acrylate, lauryl(meth)acrylate, arrachinyl(meth)acrylate, behenyl(meth)acrylate, lignocerenyl(meth)acrylate, cerotinyl(meth)acrylate, melissinyl(meth)acrylate, palmitoleinyl(meth)acrylate, oleyl(meth)acrylate, linolyl(meth)acrylate, linolenyl(meth)acrylate and mixtures thereof.

The monomers a3) are polymerized into the polymers A) prepared according to the invention in an amount in the range from 0-20% by weight, preferably in the range from 0.1-10% by weight, based on the total amount of all monomers polymerized into the polymers A).

a4) Monomers Different from a1) to a3)

Polymer A comprises, in polymerized-in form, 0 to 20% by weight, preferably 0 to 3% by weight, particularly preferably less than 0.1% by weight, of further monomers different from a1) to a3).

In the present case, "monomers different from a1) to a3)" are to be understood as meaning all those polymerizable compounds a4) which are different from a1) to a3) and which are cosmetically acceptable in their polymerized-in form.

Polymer B

The polymer B different from polymer A comprises, in polymerized-in form, b1) at least one monomer b1) which carries at least one amide group, and b2) optionally further monomers b2) different from b1).

In one or more embodiments, the monomers b1) are selected from primary amides of α,β-ethylenically unsaturated monocarboxylic acids, N-vinylamides of saturated monocarboxylic acids, N-vinyllactams, N-alkyl- and N,N-dialkylamides of a,13-ethylenically unsaturated monocarboxylic acids and mixtures thereof.

In one or more embodiments, monomers b1) are N-vinyllactams and derivatives thereof which can have e.g. one or more alkyl substituents such as methyl, ethyl, n-propyl, isopropyl, n-butyl, sec.-butyl, tert-butyl etc. These include e.g. N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam and N-vinyl-7-ethyl-2-caprolactam.

Suitable as b1) are also N-alkyl- and N,N-dialkylamides of a,13-ethylenically unsaturated monocarboxylic acids which, in addition to the carbonyl carbon atom of the amide group, have at most 7 further carbon atoms, such as N-methyl(meth)acrylamide, N-ethyl(meth)acrylamide, N-propyl(meth)acrylamide, N-(n-butyl)(meth)acrylamide, N-tert-butyl(meth)acrylamide, n-pentyl(meth)acrylamide. n-hexyl(meth)acrylamide, n-heptyl(meth)acrylamide, N,N-dimethyl(meth)acrylamide, N,N-diethyl(meth)acrylamide, piperidinyl(meth)acrylamide, morpholinyl(meth)acrylamide and mixtures thereof.

Suitable as b1) are also N—$C_8$-$C_{30}$-alkyl- and N—($C_1$-$C_{30}$)alkyl-N—($C_8$-$C_{30}$)alkylamides, such as n-octyl(meth)acrylamide, 1,1,3,3-tetramethylbutyl(meth)acrylamide, 2-ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arachinyl(meth)acrylamide, behenyl(meth)acrylamide, lignocerenyl(meth)acrylamide, cerotinyl(meth)acrylamide, melissyl(meth)acrylamide, palmitoleinyl(meth)acrylamide, oleyl(meth)acrylamide, linolyl(meth)acrylamide, linolenyl (meth)acrylamide, stearyl(meth)acrylamide, lauryl(meth) acrylamide, N-methyl-N-(n-octyl)(meth)~crylamide.N,N-di-(n-octyl)(meth)acrylamide and mixtures thereof.

Open-chain N-vinylamide compounds suitable as monomers b1) are, for example, Nvinylformamide, N-vinyl-N-methylformamide, N-vinylacetamide, N-vinyl-Nmethylacetamide, N-vinyl-N-ethylacetamide, N-vinylpropionamide, N-vinyl-N-methylpropionamide, N-vinylbutyramide and mixtures thereof, where N-vinylformamide is preferred.

In a specific embodiment, monomers b1) are N-vinylpyrrolidone, N-vinylcaprolactam, Nvinylformamide, acrylamide and methacrylamide.

In an embodiment of the invention, b1) is or comprises methacrylamide.

As used herein the phrase "monomers b2) different from b1)" is to be understood as meaning all those compounds polymerizable with b1) which are different from b1) and which are cosmetically acceptable in their polymerized-in form.

In an embodiment of the invention, the polymer P prepared by the process according to the invention comprises the polymers A and B in a weight ratio AB in the range from 50:50 to 98:2.

In an embodiment of the invention, the polymer P prepared by the process according to the invention comprises the polymers A and B in a weight ratio A:B in the range from 2:1 to 20:1.

In an embodiment of the invention, the polymer P prepared by the process according to the invention comprises the polymers A and B in a weight ratio AB in the range from 5:1 to 10:1.

Polymerization

The polymers P are prepared according to the invention by preparing one of the polymers A or B in the presence of the other polymer in each case.

For this purpose, there are several possibilities according to the invention:

In process 1, the preparation of the second polymer is only started when the preparation of the first polymer is virtually completely concluded.

In process 1 ("in succession"), thus, for example, the polymerization of the monomers b1) and b2) is only started when the polymerization of the monomers a1) to a4) is virtually completely concluded.

In process 2 ("parallel 1"), the preparation of the second polymer is only started when at least 50% by weight of all monomers which are used for the preparation of the first polymer have been polymerized.

In process 2, thus, for example. the polymerization of the monomers b1) and b2) is started when at least 50% by weight of the total amount of the monomers a1) to a4) have been polymerized.

In process 3 ("parallel 2"), the preparation of the second polymer is only started when in the region of 10 to 50% by weight of all monomers which are used in total for the preparation of the first polymer have been polymerized, and is ended before 80% by weight of all monomers which are used for the preparation of the first polymer have been polymerized.

In process 3, thus, for example, the polymerization of the monomers b1) and b2) is started when in the region of 10 to 50% by weight of the total amount of all monomers a1) to a4) have been polymerized, and is ended before 80% by weight of the total amount of all monomers a1) to a4) have been polymerized.

Process 1: "In Succession"

One or more embodiments of the invention are directed to a process wherein the preparation of polymer A or B is only started when more than 99% by weight, preferably more than 99.9% by weight, in particular more than 99.99% by weight, of the amount of all monomers to be used for the preparation of the other polymer in each case have been polymerized.

In an embodiment of the invention, the preparation of polymer B, thus the polymerization of monomers b1) and b2), only starts when more than 99% by weight, preferably more than 99.9% by weight, in particular more than 99.99% by weight, of the amount of all monomers a1) to a4) to be used for the preparation of polymer A have been polymerized.

In a further embodiment of the invention, the preparation of polymer A, thus the polymerization of monomers a1) to a4), only starts when more than 99% by weight, preferably more than 99.9% by weight, in particular more than 99.99% by weight, of the amount of all monomers b1) and b2) to be used for the preparation of polymer B have been polymerized.

In one or more embodiments of the present invention, copolymerization of the monomers a1) to a4) with the monomers b1) and b2) takes place only to a minor extent.

Process 2: "Parallel 1"

A further embodiment of the invention is the process according to the invention wherein the preparation of polymer A or B, thus the polymerization of the monomers a1) to a4) or b1) and b2), respectively, is started when in the region of 50 to 99% by weight of all monomers to be used for the preparation of the other polymer in each case have been polymerized.

In an embodiment of the invention, the preparation of polymer A, thus the polymerization of the monomers a1) to a4), is started when in the region of 50 to 99% by weight of all monomers b1) and b2) to be used for the preparation of polymer B have been polymerized.

In an embodiment of the invention, the preparation of polymer B, thus the polymerization of the monomers b1) and b2), is started when in the region of 50 to 99% by weight of all monomers a1) to a4) to be used for the preparation of polymer A have been polymerized.

Depending on when the polymerization of the second polymer A or B is started, in this process according to the invention, a copolymerization of the monomers a1) to a4) with b1) and b2) takes place to a greater or lesser extent.

Process 3: "Parallel 2"

A further embodiment of the invention is the process according to the invention wherein the preparation of polymer A or B, thus the polymerization of the monomers a1) to a4) or b1) and b2) is only started when in the region of 10 to 50% by weight of all monomers to be used for the preparation of the other polymer in each case have been polymerized, and is ended before more than 80% by weight of the amount of all monomers to be used for the preparation of the other polymer have been polymerized.

In an embodiment of the invention, the preparation of polymer A, thus the polymerization of the monomers a1) to a4), is only started when in the region of 10 to 50% by weight of all monomers b1) and b2) to be used for the preparation of polymer B have been polymerized, and is ended before more than 80% by weight of the amount of all monomers b1) and b2) to be used for the preparation of polymer B have been polymerized.

In an embodiment of the invention, the preparation of polymer B, thus the polymerization of the monomers b1) and b2), is only started when in the region of 10 to 10 50% by weight of all monomers a1) to a4) to be used for the preparation of polymer A have been polymerized, and is ended before more than 80% by weight of the amount of all monomers a1) to a4) to be used for the preparation of polymer A have been polymerized.

A specific embodiment of the invention is the process according to the invention in which the preparation of polymer B, thus the polymerization of the monomers b1) and b2), is started when more than 99% by weight, preferably more than 99.9% by weight, in particular more than 99.99% by weight, of the amount of all monomers a1) to a4) to be used for the preparation of polymer A have been polymerized.

A specific embodiment of the invention is thus directed to a process for the preparation of polymers P, the process comprising polymerizing at least one polymer A and at least one polymer B, wherein (A) Polymer A comprises, in polymerized-in form:
   a1) 30 to 70% by weight of $C_1$-$C_4$-alkyl(meth)acrylate,
   a2) 30 to 70% by weight of (meth)acrylic acid,
   a3) 0 to 20% by weight of $C_8$-$C_{30}$-alkyl-substituted monomers, and
   a4) 0 to 20% by weight of further monomers different from a1) to a2), where the amounts of a1) to a4) add up to 100% by weight; and (B) Polymer B comprises, in polymerized-in form:
   b1) at least one monomer b1) which carries at least one amide group, and
   b2) optionally further monomers b1) different from b1),
wherein the polymerization of monomers b1) and b2) is only started when more than 99% by weight of the amount of all monomers a1) to a4) to be used for the preparation of polymer A have been polymerized A specific embodiment of the invention is directed to a process for the preparation of polymers P, the process comprising polymerizing at least one polymer A and at least one polymer B, wherein (A) Polymer A comprises, in polymerized-in form:
   a1) 40 to 60% by weight of $C_1$-$C_4$-alkyl(meth)acrylate,
   a2) 35 to 59% by weight of (meth)acrylic acid,
   a3) 0.1 to 10% by weight of $C_8$-$C_{30}$-alkyl-substituted monomers, and
   a4) 0 to 3% by weight of further monomers different from a1) to a2),
where the amounts of a1) to a4) add up to 100% by weight; and (B) Polymer B comprises, in polymerized-in form:
   b1) at least one monomer b1) which carries at least one amide group, and
   b2) optionally further monomers b1) different from b1),
wherein the polymerization of the monomers b1) and b2) is only started when more than 99% by weight of the amount of all monomers a1) to a4) to be used for the preparation of polymer A have been polymerized.

A further preferred embodiment of the invention is directed to a process for the preparation of polymers P, the process comprising polymerizing at least one polymer A and at least one polymer B, wherein (A) Polymer A comprises, in polymerized-in form:
   a1) 40 to 60% by weight of ethyl acrylate,
   a2) 35 to 59% by weight of methacrylic acid,
   a3) 0.1 to 10% by weight of monomers of the general formula a3.1)

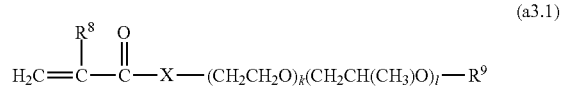

where
   k is an integer in the range from 10 to 30 and
   $R^9$ is a linear $C_{12}$-$C_{18}$-alkyl radical, and
     a4) 0 to 3% by weight of further monomers different from a1) to a2),
where the amounts of a1) to a4) add up to 100% by weight; and (B) Polymer B comprises, in polymerized-in form:
   b 1) methacrylamide, and
   b2) optionally further monomers b1) different from b1),
wherein the polymerization of the monomers b1) and b2) is only started when more than 99% by weight of the amount of all monomers a1) to a4) to be used for the preparation of polymer A have been polymerized.

In one or more embodiments, the process according to the invention is a radical polymerization. The process according to the invention can be carried out for example as solution polymerization, precipitation polymerization or emulsion polymerization. The emulsion polymerization is described for example in H. Rauch-Puntigam, Th. Völker, Acryl-und Methacrylverbindungen, [Acrylic and methacrylic compounds], Springer Verlag, Berlin, 1967.

In one or more embodiments, the process according to the invention is an aqueous radical emulsion polymerization. This is carried out in the presence of ionic or nonionic emulsifiers for emulsifying and for stabilizing the resulting polymer B.

Radical Starters

Radical starters (initiators), which can be used, are the substances known to the person skilled in the art. Suitable radical starters are described, for example, in WO 2007/017434, p. 31, 1. 28 to p. 32, 1. 22, to which reference is hereby made. The radical starters are preferably used in amounts in the range from 0.02 to 2% by weight, based on the total amount of the polymerizable monomers a1) to a4) and b1) to b2), of 100% by weight.

The process according to the invention is can be carried out at temperatures of from 30 to 100° C.

Molecular Weight Regulators

In an embodiment of the invention, so-called molecular weight regulators are used to regulate the molecular weight of the polymers. Molecular weight regulators are compounds with radical-transferring properties. Preferred molecular weight regulators are mercaptans such as e.g. 2-ethylhexyl thioglycolate, n-butylmercaptan, n- and t-dodecylmercaptan or pentaerythritol tetrathioglycolate. Further suitable molecular weight regulators are described in WO 2007/017434, p. 32, 1. 27 to p. 33, 1. 21, to which reference is hereby made.

Neutralization

The acid groups of the polymers prepared according to the invention can be present in protonated form, I.e. nonionic form, or partially or completely deprotonated form, I.e. ionic form. Particularly for using the polymers in hair cosmetic preparations, a partial or complete neutralization of the acid groups is advantageous.

The at least partial neutralization of the acid groups of polymers P prepared according to the invention can take place by reaction with the bases known to the person skilled in the art, such as alkali metal hydroxides, ammonia or amines.

Neutralizing agents suitable according to the invention are described in WO 2007/024457, p. 17, 1. 4 to 1. 40, to which reference is hereby made.

Preferred neutralizing agents are 2-amino-2-methylpropanol, triethanolamine, 2-amino-2-ethylpropane-1,3-diol, N,N-dimethylaminoethanol or 3-diethylamino-1-propylamine.

Crosslinkers

In an embodiment of the invention, so-called crosslinkers are used for the preparation of the polymers B by the process according to the invention. Suitable crosslinkers are described in WO 20071024457, p. 7. 1. 1 to p. 9. 1. 2, to which reference is hereby made.

The polymers P obtainable by the process according to the invention are also in accordance with the invention.

Also in accordance with the invention is the use of a polymer P according to the invention as a thickener, preferably as a thickener for cosmetic preparations, in particular as thickener for hair cosmetic preparations.

Also provided by the invention is a method of treating hair, wherein the hair is brought into contact with a polymer P according to the invention.

Apart from in the area of the cosmetic preparations, the polymers according to the invention are suitable, on account of their thickening effect in aqueous systems and their film-forming properties, for use as adhesives, binders and setting agents in numerous further fields of application.

For example, the polymers according to the invention are suitable as pharmaceutical auxiliaries, such as tablet binders, thickeners. electrogels or skin adhesion gels and detergent additives such as thickeners, soil release, and also as auxiliaries for numerous technical applications such as adhesives (thickeners for adhesive sticks), paper (paper auxiliaries, thickeners for colored paper slips), pigment dispersions, textile auxiliaries, ion exchangers, tertiary recovery of petroleum and in particular also crop protection preparations.

It is also provided by the invention to isolate the polymers P according to the invention as solids by means of known processes, for example by spray drying the polymers P prepared by emulsion polymerization.

The polymer powders obtained in this way are easy to transport and to store and can be incorporated into corresponding preparations.

Cosmetic Preparations

Also provided by the invention are cosmetic preparations, preferably hair cosmetic preparations, comprising a polymer P obtainable by the process according to the invention.

The invention also relates to cosmetic preparations which comprise the polymers P obtainable by the process according to the invention.

Such cosmetic preparations according to the invention are selected, for example, from gel creams, hydro-formulations, stick formulations, cosmetic oils and oil gels, mascara, self-tanning compositions, face care compositions, body care compositions, after-sun preparations, hair shaping compositions and hair setting compositions.

Further cosmetic preparations according to the invention are skin cosmetic preparations, in particular those for skin-care. These are present in particular as W/O or O/W skin creams, day and night creams, eye creams, face creams, anti-wrinkle creams, mimic creams, moisturizing creams, bleaching creams, vitamin creams, skin lotions, care lotions and moisturizing lotions.

Furthermore, the polymers P are suitable as ingredients for skin cosmetic preparations such as face tonics, face masks, deodorants and other cosmetic lotions and for use in decorative cosmetics, for example as concealing stick, stage make-up, in mascara and eye shadows, lip pencils, kohl pencils, eyeliners, make-up, foundations, blushers and powders and eyebrow pencils.

Moreover, the polymers P can be used in nose strips for pore cleansing, in anti-acne compositions, repellents, shaving compositions, hair removal compositions, intimate care compositions, foot care compositions, and also in baby care.

Further preferred preparations according to the invention are washing, showering and bathing preparations which comprise the polymers P.

Within the context of this invention, washing, showering and bathing preparations are understood as meaning soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, showering and bathing preparations, such as washing lotions, shower baths and shower gels, foam baths, oil baths and scrub preparations, shaving foams, shaving lotions and shaving creams.

The cosmetic preparations according to the invention can be in the form of aqueous or aqueous-alcoholic solutions, O/W and W/O emulsions, hydrodispersion formulations, solids-stabilized formulations, stick formulations, PIT formulations, in the form of creams, foams, sprays (pump spray or aerosol), gels, gel sprays, lotions, oils, oil gels or mousse, and be formulated accordingly with customary further auxiliaries.

The cosmetic preparations according to the invention preferably comprise at least one polymer P, at least one cosmetically acceptable carrier and at least one constituent different therefrom which is selected from cosmetically active ingredients, emulsifiers, surfactants, preservatives, perfume oils, further thickeners, hair polymers, hair and skin conditioning agents, graft polymers, water-soluble or dispersible silicone-containing polymers, photoprotective agents, bleaches, gel formers, care agents, colorants, tinting agents, tanning agents, dyes, pigments, consistency regulators, humectants. Refatting agents, collagen, protein hydrolyzates, lipids, antioxidants, antifoams, antistats, emollients and softeners.

Hair care compositions preferred according to the invention are selected from pretreatment compositions, hair rinses, hair conditioning agents, hair balsams, leave-on hair treatments rinse-off hair treatments, hair tonics, pomades, styling creams, styling lotions, styling gels, end fluids, hot-oil treatments and foam treatments.

The polymers P are preferably used as rheology-modifying film formers, hair-setting compositions and conditioning agents for producing cosmetic, preferably hair cosmetic, preparations.

The invention thus further provides cosmetic, in particular hair cosmetic, preparations comprising at least one polymer P.

Preferred hair cosmetic preparations are hair cleansing compositions, shampoos, hair care compositions, hair coloring preparations and hair setting compositions, including in particular hair setting gels.

The polymers P act in particular as film-forming and/or conditioning rheology modifiers.

They are thus suitable specifically for hair setting compositions as "thickening setters" or "setting thickeners" and in hair care compositions as "conditioning thickeners".

In principle, the polymers P, when used in multiphase preparations such as, for example, O/W and W/O, can be used either in the water phase or in the oil phase. In general, heterogeneous-phase liquid/liquid preparations comprise the polymers P essentially in the water phase.

The invention further provides hair cosmetic compositions comprising
- A) at least one polymer P,
- B) optionally at least one hair polymer different from A),
- C) at least one cosmetically acceptable carrier, and
- D) optionally at least one cosmetically acceptable active ingredient and/or auxiliary different from A) and B).

The polymers P in the hair cosmetic compositions also be used as hair setting component, meaning that the use of further setting polymers is required only in a reduced amount or may even be entirely superfluous.

The polymers P are advantageously also characterized by conditioning properties and can improve the sensory properties of the hair, e.g. give it suppleness and shine.

The hair cosmetic compositions comprise the polymers P preferably in a fraction of from about 0.1 to 10% by weight, particularly preferably 0.2 to 6% by weight, in particular 0.3 to 3% by weight, based on the total weight of the composition.

Examples of suitable hair polymers B) and their preferred amounts are described in detail in WO 2007/010035, p. 68, l. 32 to p. 70, l. 22. Reference is hereby made to this passage in its entirety.

Preferably, the preparations have a carrier component C) which is selected from water, hydrophilic components, hydrophobic components and mixtures thereof.

Suitable carrier components C) are described in detail in WO 2007/010035, p. 70, l. 28 to p. 71, l. 37. Reference is hereby made to this passage in its entirety.

Additionally, the compositions according to the invention can comprise, as component D), at least one further cosmetic active ingredient or auxiliary different from A) and B).

Suitable components D) are described in detail in WO 2007/010035, p. 72, l. 2 to p. 72, l. 13. Reference is hereby made to this passage in its entirety.

The polymers P can be used together with known thickeners. Suitable thickeners are described in detail in WO 2007/010035, p. 72, l. 15 to p. 72, l. 24. Reference is hereby made to this passage in its entirety.

Conditioning Agents

The conditioning agents selected for the cosmetic preparations according to the invention are preferably those conditioning agents which are described on page 34, line 24 to page 37, line 10 of WO 2006/106140, to which reference is hereby made.

Thickeners

Thickeners suitable for gels, shampoos and hair care compositions are given in "Kosmetik und Hygiene von Kopf bis Fuβ [Cosmetics and Hygiene from Head to Toe]", ed. W. Umbach, 3rd edition, Wiley-VCH, 2004, pp. 235-236, to which reference is made at this point in its entirety.

Suitable further thickeners for the cosmetic preparations according to the invention are described for example also on page 37, line 12 to page 38, line 8 of WO 2006/106140, to which reference is hereby made.

Preservatives

Suitable preservatives for the cosmetic preparations according to the invention are described, for example, on page 38, line 10 to page 39, line 18 of WO 2006/106140, to which reference is hereby made.

UV Photoprotective Filters

Suitable UV-photoprotective filters for the cosmetic preparations according to the invention are described for example on page 39, line 20 to page 41, line 10 of WO 2006/106140, to which reference is hereby made.

Antioxidants

Suitable antioxidants for the cosmetic preparations according to the invention are described, for example, on page 41, line 12 to page 42, line 33 of WO 2006/106140, to which reference is hereby made.

Dispersants

If insoluble active ingredients, e.g. antidandruff active ingredients or silicone oils, are to be dispersed and held permanently in suspension in the preparations according to the invention, preference is given to using dispersants and thickeners such as e.g. magnesium aluminum silicates, bentonites, fatty acyl derivatives, polyvinylpyrrolidone or hydrocolloids, e.g. xanthan gum or carbomers.

The preparations can comprise further additives customary in cosmetics, for example perfume, dyes, refatting agents. complexing and sequestering agents, pearlescent agents, plant extracts, vitamins, active ingredients, pigments which have a coloring effect, softening, moisturizing and/or humectant substances, or other customary constituents such as alcohols, polyols, polymers, organic acids for adjusting the pH, foam stabilizers, electrolytes, organic solvents or silicone derivatives.

With regard to said further ingredients known to the person skilled in the art for the preparations, reference may be made to "Kosmetik and Hygiene von Kopf bis Fuβ." [Cosmetics and Hygiene from Head to Toe]", ed. W. Umbach, 3rd edition, Wiley-VCH, 2004, pp. 123-128, to which reference is hereby made.

The preparations according to the invention such as hair sprays, gels, shampoos and hair care compositions comprise optionally ethoxylated oils selected from the group of ethoxylated glycerol fatty acid esters, particularly preferably PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil. jojoba oil ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid glycerides, PEG-10 olive oil glycerides, PEG-13 40 sunflower oil glycerides, PEG-7 hydrogenated castor oil. hydrogenated palm kernel oil glyceride PEG-6 ester, PEG-20 corn oil glycerides, PEG-18 glyceryl oleate cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-80 glyceryl cocoate, PEG-60 almond oil glycerides, PEG-60 "evening primrose" glycerides, PEG-200 hydrogenated glyceryl palmate, PEG-90 glyceryl isostearate.

Preferred ethoxylated oils are PEG-7 glyceryl cocoate, PEG-9 cocoglycerides, PEG-40 hydrogenated castor oil, PEG-200 hydrogenated glyceryl palmate.

Ethoxylated glycerol fatty acid esters are used for various purposes in aqueous cleansing formulations. Glycerol fatty acid esters with a degree of ethoxylation of ca. 30-50 serve as solubility promoters for nonpolar substances such as perfume oils.

Highly ethoxylated glycerol fatty acid esters are used as thickeners.

Active Ingredients

Advantageous active ingredients for the cosmetic preparations according to the invention are described, for example on page 44, line 24 to page 49, line 39 of WO 2006/106140, to which reference is hereby made.

UV Photoprotective Agents

In a preferred embodiment, the preparations according to the invention comprise UV photoprotective agents for protecting the skin and/or the hair. Suitable UV photoprotective agents are described in detail in WO 2006/106114, p. 24, 1. 4 to p. 27, 1. 27, to which reference is hereby made in its entirety.

Pearlescent Waxes

Suitable pearlescent waxes for the cosmetic preparations according to the invention are described for example on page 50, line 1 to line 16 of WO 2006/106140, to which reference is hereby made.

Emulsifiers

In a preferred embodiment of the invention, the cosmetic preparations according to the invention are present in the form of emulsions. The preparation of such emulsions takes place by known methods. Suitable emulsifiers for the emulsions according to the invention are described for example on page 50, line 18 to page 53, line 4 of WO 2006/106140, to which reference is hereby made.

Perfume Oils

If perfume oils are to be added to the cosmetic preparations according to the invention, then suitable perfume oils are described, for example, on page 53, line 10 to page 54, line 3 of WO 2006/106140, to which reference is hereby made.

Pigments

The cosmetic preparations according to the invention optionally further comprise pigments. Suitable pigments for the preparations according to the invention are described for example on page 54, line 5 to page 55, line 19 of WO 2006/106140, to which reference is hereby made.

Nanoparticles

The preparations according to the invention optionally comprise water-insoluble nanoparticles, i.e. particles with a particle size in the range from 1 to 200, preferably from 5 to 100 nm. Preferred nanoparticles are nanoparticles of metal oxides, in particular of zinc oxide and/or titanium dioxide.

Polymers

In a preferred embodiment, the cosmetic preparations according to the invention also comprise further polymers apart from the polymers P. Suitable further polymers are described for example on page 55, line 21 to page 63, line 2 of WO 2006/106140. Reference is hereby made to the content of the cited passage in its entirety.

The polymers P are also suitable as rheology-modifying film formers in hair gels, in particular so-called styling gels.

A preferred embodiment of the invention is hair cosmetic preparations, in particular hair setting compositions and hair gels, which, besides the polymers obtainable according to the invention, comprise gel formers customary in cosmetics.

Such further customary gel formers are lightly crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglycerides, sodium acrylates copolymer, polyquaternium-32 (and) paraffinum liquidum (INCI), sodium acrylates copolymer (and) paraffinum liquidum (and) PPG-1 trideceth-6, acrylamidopropyltrimonium chloride/acrylamide copolymer, steareth-10 allyl ether acrylates copolymer, polyquaternium-37 (and) paraffinum liquidum (and) PPG-1 trideceth-6, polyquaternium-37 (and) propylene glycol 30 dicaprate dicaprylate (and) PPG-1 trideceth-6, polyquaternium-7, polyquaternium-44.

Hair Washing Compositions

A preferred embodiment of the invention is hair washing compositions and shampoos comprising the polymers P.

Depending on hair condition or scalp problem, optionally additional requirements are placed on shampoos and hair washing compositions.

Preferred shampoos and hair washing compositions according to the invention comprise anionic surfactants. Further preferred shampoos and hair washing compositions according to the invention comprise combinations of anionic and ampholytic surfactants. Further preferred shampoos and hair washing compositions according to the invention comprise combinations of anionic and zwitterionic surfactants. Further preferred shampoos and cosmetic cleansing compositions according to the invention comprise combinations of anionic and nonionic surfactants.

Suitable surfactants of all types have already been described above under "Surfactants".

Preferred anionic surfactants are alkyl sulfates, alkyl polyglycol.ether sulfates and ether carboxylic acid salts having. 10 to 18 carbon atoms in the alkyl group and up to 12 glycol ether groups in the molecule and sulfosuccinic acid mono- and dialkyl esters having 8 to 18 carbon atoms in the alkyl group and sulfosuccinic acid monoalkyl polyoxyethyl esters having 8 to 18 carbon atoms in the alkyl group and 1 to 6 oxyethyl groups. Particularly preferred anionic surfactants are the alkali metal or ammonium salts of lauryl ether sulfate with a degree of ethoxylation from 2 to 4 EO units.

A preferred zwitterionic surfactant is the fatty acid amide derivative known under the INCI name Cocamidopropyl Betaine.

Particularly preferred ampholytic surfactants are N-cocoalkyl aminopropionate, cocoacylaminoethyl aminopropionate and C12-C12-acylsarcosine.

Preferred nonionic surfactants have proven to be the alkylene oxide addition products onto saturated linear fatty alcohols and fatty acids having in each case 2 to 30 mol of ethylene oxide per mole of fatty alcohol or fatty acid. Preparations with excellent properties are likewise obtained if they comprise fatty acid esters of ethoxylated glycerol as nonionic surfactants.

Presentation

The preparations according to the invention can be present, for example, as preparations that can be sprayed form aerosol containers, squeezable bottles or through a pump, spray or foaming device, but also in the form of a composition that can be applied from standard bottles and containers. Suitable propellants for cosmetic or dermatological preparation according to the invention that can be sprayed from aerosol containers are the customary known readily volatile, liquefied propellants, for example dimethyl ether, hydrocarbons (propane, butane, isobutane), which can be used on their own or in a mixture with one another, for example mixtures of dimethyl ether and isobutane or dimethyl ether and butane. Compressed air, nitrogen, nitrogen dioxide or carbon dioxide or mixtures of these substances can also be used advantageously.

The preparations according to the invention can be prepared in the customary manner by mixing the individual constituents. The pH of the preparations can be adjusted in a known manner by adding acids or bases, preferably by adding buffer mixtures, e.g. based on citric acid/citrate or phosphoric acid/phosphate buffer mixtures. In one embodiment of the invention, the pH is below 10, e.g. in the range from 2-7, in particular in the range from 3-5.

Preferred shampoo formulations comprise
a) 0.05 to 10% by weight of at least one polymer obtainable according to the invention,
b) 25 to 94.95% by weight of water,
c) 5 to 50% by weight of surfactants, d) 0 to 5% by weight of a conditioning agent.

e) 0 to 10% by weight of further cosmetic constituents.

In a further embodiment, by using the polymers P it is also possible to prepare surfactant-reduced formulations with less than 10% by weight of surfactant, based on the preparation, in a viscosity adequate for the preparation.

All anionic, neutral, amphoteric or cationic surfactants customarily used in shampoos and cosmetic cleansing compositions can be used in the shampoos and cosmetic cleansing compositions. Suitable surfactants have been specified above. Particular preference is given to shampoos and cosmetic cleansing compositions with a surfactant content of more than 10% by weight.

In the shampoo formulations, further conditioning agents can be used to achieve certain effects. These include, for example, cationic polymers with the INCI name Polyquaternium, in particular copolymers of vinylpyrrolidone/N-vinylimidazolium salts (Luviquat®FC, Luviquat®HM, Luviquat®MS, Luviquat®Care), copolymers of N-vinylpyrrolidone/dimethylaminoethyl methacrylate, quaternized with diethyl sulfate (Luviquat®PQ 11), copolymers of N-vinylcaprolactam/N-vinylpyrrolidone/N-vinylimidazolium salts (Luviquat®Hold); cationic cellulose derivatives (Polyquaternium-4 and -10), acrylamide copolymers (Polyquaternium-7).

Advantageous conditioning agents are, for example, the compounds referred to in accordance with INCI as Polyquaternium (in particular Polyquaternium-1 to Polyquaternium-87).

The invention is described in more detail below by examples, without limiting it thereto.

Unless stated otherwise, quantitative data in "%" are percent by weight.

Carrying Out the Flexural Test
Preparation of the Samples:

The polymer to be tested was incorporated into a gel formulation. 50 g of the prepared gel were made up to 220 g with demineralized water and dissolved. The weighed, dry hair tresses (ca. 3 g, 24 cm in length) were immersed into the dilute gel mass.

Immersion, removal and wiping three times ensured a uniform distribution.

The excess mass was wiped off between thumb and index finger, the hair tresses were then adjusted to a weight increase of 1-1.4 g (based on the starting weight of the hair 15 tress, depending on the viscosity of the mass) by squeezing between filter paper. The tresses were then shaped by hand such that they had a round cross section. At 20° C. and 65% relative humidity, the tresses were dried overnight in a climatically controlled room.

Testing the Flexural Strength:

The tests were carried out in a climatically controlled room at 20° C. and 65% relative humidity using tensile/pressure testing equipment (model Easytest 86 802, Frank).

The hair tress was placed symmetrically on two cylindrical rollers (diameter 4 mm, gap=90 mm) of the sample holder. Exactly in the middle, a rounded punch was then used to bend the tress ea. 40 mm from above until breakage of the gel film. The force required for this was measured using a weighing cell (50 N) and given in Newtons.

Determination of the Viscosity

The viscosity was measured using a viscometer of the type Brookfield DV-II+Pro at 20° C. For the measurement, spindle NO.6 was used at 20 rpm. The viscosity determination was carried out on the neutralized dispersion.

Example 1

Polymerization of methacrylamide in the presence of a copolymer of ethyl acrylate, methacrylic acid and a methacrylic acid ester of an ethoxylated C16-C18-fatty alcohol mixture.

Start of the polymerization of monomer b1) after more than 99% by weight of the monomers a1) to a4) have been polymerized.

The experimental set-up consisted of a 2 liter reaction vessel with anchor stirrer, reflux condenser and feed vessels.

In the receiver, 260.0 g of demineralized water, 0.6 9 of sodium dodecylsulfate, 6.0 g of 5 methacrylic acid and 9.0 9 of ethyl acrylate were heated to 80° C. with stirring (120 rpm).

Upon reaching 80° C., 24.0 9 of a 2.5% strength aqueous sodium peroxodisulfate solution were quickly added for the start of the reaction.

5 min after the addition of the sodium peroxodisulfate solution, a stirred emulsion consisting of:

140.0 g of demineralized water
1.65 g of sodium dodecylsulfate
7.2 g of sorbitan tristearate-20 EO (Tween®80, Croda)
25.0 g of methacrylic acid ester of an ethoxylated C16-C18-fatty alcohol mixture (Visiomer®C18 PEG-1105-MA 60% strength, Evonik)
109.0 g of methacrylic acid
126.0 g of ethyl acrylate was metered into the reaction vessel over 1.5 hours.

After the end of the emulsion feed, a feed comprising 200.0 9 of a 15% strength by weight aqueous methacrylamide solution was metered into the reaction vessel over 30 min.

After the end of the feed, the experiment was after-stirred for a further 2 h at 80° C.

The experiment was then cooled to room temperature. Upon reaching 40° C. during the cooling process, 0.9 9 of a 1% strength aqueous hydrogen peroxide solution was added.

5 min after this addition, 30.0 g of aqueous 0.25% strength by weight L(+)-ascorbic acid were metered in over 30 min.

The dispersion was then filtered over a 120 μm filter.

The pH of the 29.7% strength by weight dispersion was ca. 2.9.

This dispersion was used to formulate a gel with a fraction of 1.5% by weight of the dispersion (only solids fraction calculated)

10.1 g of dispersion from Example 1
166.0 g of demin. water
20.0 g of Luviskol®K90 (BASF SE)
0.2 g of perfume oil "Lisa" (Drom Fragrances)
0.8 g of Cremophor®CO 40 (BASF SE)
1.0 g of Euxyl®PE 9010 (Schülke+Mayr)

This formulation was adjusted with stirring to pH 7.0 with triethanolamine.

Flexural test: 209 cN
Viscosity: 45 500 mPas

Example 2

Polymerization of methacrylamide in the presence of a copolymer of ethyl acrylate, methacrylic acid and a methacrylic acid ester of an ethoxylated C16-C18-fatty alcohol mixture- Start of the polymerization of monomer b1) after in the region of 50-99% by weight of the monomers a1) to a4) have been polymerized.

The experimental set-up consisted of a 2l reaction vessel with anchor stirrer, reflux condenser and feed vessels.

In the receiver, 190.0 g of demin. water, 0.6 g of sodium dodecylsulfate, 6.0 g of methacrylic acid and 9.0 g of ethyl acrylate were heated to BO° C. with stirring (120 rpm).

Upon reaching 80° C., 24.0 g of a 2.5% strength by weight aqueous sodium peroxodisulfate solution were quickly added for the start of the reaction.

5 min after the addition, a stirred emulsion consisting of:
210.0 g of demin. water
1.65 g of sodium dodecylsulfate
7.2 g of sorbitan tristearate-20 EO (Tween®80, Croda)
25.0 g of methacrylic acid ester of an ethoxylated C16-C18-fatty alcohol mixture (Visiomer®C18 PEG-1105-MA 60% strength, Evonik)
109.0 g of methacrylic acid
126.0 g of ethyl acrylate
was metered into the reaction vessel over 1 h 30 min.

1 h 15 min after the start of the emulsion feed, a feed comprising 200.0 g of a 15% strength by weight aqueous methacrylamide solution was run into the reaction vessel over 30 min.

After the end of the feed, the experiment was after-stiffed for a further 2 h at 80° C. The experiment was then cooled to room temperature. Upon reaching 40° C. during the cooling process, 0.9 g of a 1% strength by weight aqueous hydrogen peroxide solution was added. 5 min after this addition, 30.0 g of aqueous 0.25% strength by weight L(+)-ascorbic acid were metered in over 30 min.

The dispersion was then filtered over a 120 μm filter.

The pH of the 29.7% strength by weight dispersion was ca. 2.9.

This dispersion was used to formulate a gel with a fraction of 1.5% by weight of the dispersion (only solids fraction calculated)
9.9 g of dispersion Example 2
166.1 g of demin. water
20.0 g of Luviskol®K90 (BASF SE)
0.2 g of perfume oil "Lisa" (Drom Fragrances)
0.8 g of Cremophor®CO 40 (BASF SE)
1.0 g of Euxyl®pE 9010 (Schülke+Mayr GMBH)
This formulation was adjusted with stirring to pH 7.0 with triethanolamine.
Flexural test: 212 cN
Viscosity: 66000 mPas Comparative Example Simultaneous polymerization of methacrylamide, ethyl acrylate, methacrylic acid and a methacrylic acid ester of an ethoxylated C16-C18-fatty alcohol mixture The experimental set-up consisted of a 2 l reaction vessel with anchor stirrer, reflux condenser and feed vessels.

In the receiver, 360.0 g of demineralized water, 0.6 g of sodium dodecylsulfate, 6.0 g of methacrylic acid and 9.0 g of ethyl acrylate were heated to 80° C. with stirring (120 rpm).

Upon reaching 80° C., 24.0 9 of a 2.5% strength by weight aqueous sodium peroxodisulfate solution were quickly added for the start of the reaction. 5 min after the addition, a stirred emulsion consisting of:
40.0 g of demin. water
1.65 g of sodium dodecylsulfate
7.2 g of sorbitan tristearate-20 EO (Tween®BO, Croda)
25.0 g of methacrylic acid ester of an ethoxylated C16-C18-fatty alcohol mixture 30 (Visiomer®C1B PEG-1105-MA 60% strength, Evonik)
200.0 g of methacrylamide (15% strength in water)
109.0 g of methacrylic acid
126.0 g of ethyl acrylate
was metered into the reaction vessel over 1.5 h.

After the end of the feed, the experiment was after-stirred for a further 2 h at 80° C. The experiment was then cooled to room temperature. Upon reaching 40° C. during the cooling process, 0.9 g of a 1% strength by weight aqueous hydrogen peroxide solution was added. 5 min after this addition, 30.0 9 of aqueous 0.25% strength by weight L(+)-ascorbic acid were metered in over 30 min. The dispersion was then filtered over a 120 μm filter.

The pH of the 31.6% strength dispersion was ca. 2.9.

This dispersion was used to formulate a gel with a fraction of 1.5% by weight of the dispersion (only solids fraction calculated)
9.5 g of dispersion comparative example
166.4 g of demin. water
20.0 g of Luviskol®K90 (BASF SE)
0.2 g of perfume oil "Lisa" (Drom Fragrances)
0.8 g of Cremophor®CO 40 (BASF SE)
1.0 g of Euxyl®pE 9010 (Schülke+Mayr)
This formulation was adjusted with stirring to pH 7.0 with triethanolamine.
Flexural test 1: 167cN
Viscosity 2: 67 700 mPas
Result:

|  | Example 1 | Example 2 | Comparative Example |
|---|---|---|---|
| Flexural Rigidity [cN] | 209 | 212 | 167 |
| Thickening Power [mPa * s] | 45 500 | 66 000 | 67 700 |

A thickening power adequate for gel formulations is at least 40000 mPa*s, the value for the flexural rigidity should be at least 190 cN.

Hair Gels

The hair gels according to the invention presented below are prepared as follows: firstly, the components of phase A are solubilized. Phase B is then prepared and 5 dissolved, then added to phase A, and a common solution is prepared with stirring. Finally, phase C is added to phase A+B and stirred until homogeneous.

The stated amounts are in % by weight unless expressly described otherwise.

Dispersion 1 is the filtered polymer dispersion of example 1 according to the invention.

Instead of dispersion 1, in all of the following formulations, any desired polymer 10 dispersion according to the invention can be used, in particular also the polymer dispersion of Example 1 according to the invention.

Hair Gel 1

| Ingredient | INCI (manufacturer) |
|---|---|
| Phase A | |
| 0.40 Cremophor ® CO40 | PEG-40 Hydrogenated Castor Oil |
| 0.10 Perfume oil | |
| 81.09 Water dist. | Aqua dem. |
| Phase B | |
| 25 15.00 Luviskol ® K90 (3% polymer content) | PVP |
| 2.57 Dispersion 1 (0.8% WS) | |
| 0.50 Euxyl ® PE 9010 | Phenoxyethanol Ethylhexyl Glycerin |
| Phase C | |
| 0.34 AMP | 2-Amino-2-Methyl-propanol |

Hair Gel 2

| Ingredient | INCI (manufacturer) |
|---|---|
| Phase A | |
| 0.40 Cremophor ® CO40 | PEG-40 Hydrogenated Castor OIl |
| 0.10 Perfume oil | |
| 85.45 Water dist. | Aqua dem. |
| Phase B | |
| 10.00 Luviskol ® l VA64W (5% polymer content) | PVPNA |
| 3.21 Dispersion 1 (1.0% polymer content) | |
| 0.50 Euxyl ® PE 9010 | Phenoxyethanol Ethylhexyl Glycerin |

Hair Gel 3

| Ingredient | INCI (manufacturer) |
|---|---|
| Phase A | |
| 0.40 Cremophor ® CO40 | PEG-40 Hydrogenated Castor Oil |
| 0.10 Perfume oil | |
| 80.45 Water dist. | Aqua dem. |
| Phase B | |
| 15.00 Luviset ® Clear (3% polymer content) | VP/Methacrylamide/N-Vinyl Imidazole Polymer |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | 2-Amino-2-Methyl-propanol |

Hair Gel 4

| Ingredient | INCI (manufacturer) |
|---|---|
| Phase A | |
| 0.40 Cremophor ® CO40 | PEG-40 Hydrogenated Castor Oil |
| 0.10 Perfume oil | |
| 85.45 Water dist. | Aqua dem. |
| Phase B | |
| 2.50 Luviquat ® Supreme (0.5% polymer content) | Polyquaternium-68 |
| 7.50 Luviset ® Clear (1.50% polymer content) | VP/Methacrylamide/N-Vinyl Imidazole Polymer |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | 2-Amino-2-Methyl-propanol |

Hair Gel 5

| Ingredient | INCI (manufacturer) |
|---|---|
| Phase A | |
| 0.40 Cremophor ® CO40 | PEG-40 Hydrogenated Castor Oil |
| 0.10 Perfume oil | |
| 77.95 Water dist. | Aqua dem. |
| Phase B | |
| 2.50 Luvjquat ® Supreme (0.5% polymer content) | Polyquaternium-68 |
| 15.00 Luviskol ® K90 (3.0% polymer content) | PVP |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | 2-Amino-2-Methyl-propanol |

Hair Gel 6

| Ingredient | INCI (manufacturer) |
|---|---|
| Phase A | |
| 0.40 Cremophor ® CO40 | PEG-40 Hydrogenated Castor Oil |
| 0.10 Perfume oil | |
| 82.95 Water dist. | Aqua dem. |
| Phase B | |
| 2.50 Luviquat ® Supreme (0.5% polymer content) | Polyquaternium-68 |
| 1.00 Luviskol ® VA64 (5.0% polymer content) | PVPNA |
| 3.21 Dispersion 1 (1.0% polymer content) | |
| 0.50 Euxyl ® PE 9010 | Phenoxyethanol Ethylhexyl Glycerin |
| Phase C | |
| 0.34 AMP | 2-Amino-2-Methyl-propanol |

Hair Gel 7

| Ingredient | INCI (manufacturer) |
|---|---|
| Phase A | |
| 0.30 Cremophor ® CO40 | PEG-40 Hydrogenated castor oil |
| 0.10 Perfume oil | |
| 79.84 Water dist. | Aqua dem. |
| Phase B | |
| 10.00 Luviset ® Clear (2.0% polymer content) | VP/Methacrylamide/N-Vinyl Imidazole Polymer |
| 3.33 Dispersion 1 (1.0% polymer content) | |
| 2.50 Karion ® F | Sorbitol |
| 2.50 1,2 Propylene glycol Care | Propylene glycol |
| 0.50 Panthenol 50P | Panthenol |
| 0.10 Niacinamide | Niacinamide (Nutrilo) |
| 0.50 Euxyl ® PE 9010 | |
| Phase C | |
| 0.33 AMP | 2-Amino-2-Methyl-propanol |

Hair Gel 8

| Ingredient | INCI (manufacturer) |
|---|---|
| Phase A | |
| 0.30 Cremophor ® CO40 | PEG-40 Hydrogenated Castor Oil |
| 0.10 Perfume oil | |
| 74.84 Water dist. | Aqua dem. |
| Phase B | |
| 5.00 Luviskol ® A64W (2.5% polymer content) | PVP/VA Copolymer |
| 10.00 Luviset ® Clear (2.0% polymer content) | VP/Methacrylamide/N-Vinyl Imidazole Polymer |
| 3.33 Dispersion 1 (1.0% polymer content) | |
| 2.50 Karion ® F | Sorbitol |
| 2.50 1,2 Propylene glycol Care | Propylene Glycol |
| 0.50 Panthenol 50P | Panthenol |
| 0.10 Niacinamide | Niacinamide (Nutrilo) |
| 0.50 Euxyl ® pE 9010 | Phenoxyethanol Ethylhexyl Glycerin |
| Phase C | |
| 0.33 AMP | 2-Amino-2-Methyl-propanol |

Hair Shampoos

The quantities given below are in % by weight unless expressly described otherwise.

Dispersion 1 is the filtered polymer dispersion of example 1 according to the invention.

Conditioning Shampoo with Jaguar® C 13 S and Silicones

| Ingredient | INCI (manufacturer) |
|---|---|
| Phase A | |
| 0.20 Jaguar ® C 13 S | Guar Hydroxypropyltrimonium Chloride |
| 62.00 Water dist. | Aqua demo |
| Phase B | |
| 17.50 Texapon ® N 701 (12%) | Sodium laureth Sulfate |
| 5.40 Tego ® Betain L7 (1.6%) | Cocoamidopropyl Betaine (Evonik) |
| Phase C | |
| 1.60 Dispersion 1 | |
| q.s. NaOH 20% | Sodium Hydroxide |
| Phase D | |
| 2.20 Dow Corning ® Dispersion 1785 (1.3%) | Dimethiconol. TEA-Dodecylbenzenesulfonate |
| 1.10 Dow Corning ® Emulsion CE-8170 (0.2%) | Amodimethocone, C11-15 Pareth-7, Glycerin, Trideceth-12 |
| 9.10 Euperlan ® 3000 AM (2%) | Glycol Distearate. Laureth-4. Cocamidopropyl Betaine |
| 0.20 Perfume oil | |
| 0.20 Glydant ® LTD. | DMDM Hydantoin |
| q.s. Citric acid | citric acid |
| 0.50 Sodium chloride | sodium chloride |

Preparation:

The components of phase A are dissolved. Phase B is prepared and added to phase A. Phase C is added to phase A+B and the pH is adjusted to approximately 6.7 with stirring. Phase D is stirred homogeneously into the mixture A+B+C. The pH of the resulting mixture is adjusted to approximately pH 6.0 with citric acid. sodium chloride is added and everything is stirred until homogeneous.

Conditioning Shampoo with UCARE @Polymer 400C and Silicones

| Ingredient | INCI (manufacturer) |
|---|---|
| Phase A | |
| 0.20 UCARE ® Polymer JR 400 | Polyquaternium-10 |
| 62.00 Water dist. | Aqua demo |
| Phase B | |
| 17.50 Texapon ® N 701 (12%) | Sodium laureth Sulfate |
| 5.40 Tego ® Betain L7 (1.6%) | Cocoamidopropyl Betaine (Evonik) |
| Phase C | |
| 1.60 Dispersion 1 | |
| q.s. NaOH 20% | Sodium Hydroxide |
| Phase D | |
| 20 Dow Corning ® Dispersion 1785 (1.3%) | Dimethiconol, TEA-Dodecylbenzenesulfonate |
| 1.10 Dow Corning@Emulsion CE-8170 (0.2%) | Amodimethocone, C11-15 Pareth-7, Glycerin, Trideceth-12 |
| 9.10 EuperJan ® 3000 AM (2%) | Glycol Distearate, Laureth-4, Cocamidopropyl Betaine |
| 0.20 Perfume oil | |
| 0.20 Glydant@ LTD | DMDM Hydantoin |
| Phase E | |
| q.s. Citric acid | citric acid |
| 0.50 Sodium chloride | sodium chloride |

Preparation:

The components of phase A are dissolved. Phase B is prepared and added to phase A. Phase C is added to phase A+B and the pH is adjusted to approximately 6.7 with stirring. Phase D is homogeneously stirred into the mixture A+B+C. The pH of the resulting mixture is adjusted to approximately pH 6.0 with citric acid, sodium chloride is added and everything is stirred until homogeneous.

Conditioning Shampoo with Lower Surfactant Fraction

| Ingredient | INCI (manufacturer) |
|---|---|
| Phase A | |
| 3.30 Dispersion 1 | |
| 59.80 Water dist. | Aqua dem. |
| q.s. NaOH 20% | sodium hydroxide |
| Phase B | |
| 0.10 Salcare ® CS 60 | Acrylamidopropyltrimonium Chloride |
| 2.90 Water dist. | Aqua dem. |
| Phase C | |
| 25.80 Texapon ® NSO (7% surfactant fraction) | Sodium Laureth Sulfate |
| 6.80 Tego ® Betain L7 (2.0% surfactant fraction) | Cocoamidopropyl Betaine |
| 0.30 Perfume | |
| q.s. Preservative | |
| Phase D | |
| q.s. Citric acid | citric acid |
| 0.50 Sodium chloride | sodium chloride |

Preparation:

The components of phase A are weighed in and dissolved, then adjusted to a pH of approximately 6.7 with NaOH. Phase B is weighed in and dissolved, then added to phase A. The components of phase C are added to phase A+B and stirred until homogeneous. The pH is then adjusted to approximately pH 6.0 with citric acid, sodium chloride is added and the mixture is stirred until homogeneous.

Anti-Dandruff Shampoo with Zinc Pyrithione

| Ingredient | INCI (manufacturer) |
|---|---|
| Phase A | |
| 3.20 Dispersion 1 | |
| 41.00 Water dist. | |
| q.s. NaOH•20% | Sodium Hydroxide |
| Phase B | |
| 0.80 Luviquat ® Sensation (0.2% polymer fraction) | Polyquaternium-87 |
| 2.90 Water dist. | Aqua dem. |
| Phase C | |
| 35.70 Texapon ® NSO (9.7% surfactantfraction) | Sodium Laureth Sulfate |
| 12.50 Tego ® Betain L7 (3.7% surfactant fraction) | Cocoamidopropyl Betaine |
| 2.50 Zink-Pyrion ® 48% Micro (1.2% active fraction) | Zink Pyrithione |
| Phase D | |
| 0.30 Perfume | |
| q.s. Preservative | |
| Phase E | |
| q.s Citric acid | Citric Acid |

Preparation:

The components of phase A are weighed in and dissolved, then adjusted to a pH of approximately 6.7 with NaOH. Phase B is weighed in and dissolved, then added to phase A. The components of phase C are added to phase A+B and stirred until homogeneous. Phase D is then added and the resulting mixture is homogenized. Finally, the pH is adjusted to approximately pH 6.0 with citric acid.

Conditioning Shampoo with Luviguat® Sensation, Uvinul® MC 80

| Ingredient | INCI (manufacturer) |
|---|---|
| Phase A | |
| 2.00 Luviquat ® Sensation (0.5% polymer fraction) | Polyquaternium-87 |
| 48.30 Water dist. | Aqua dem. |
| q.s. Preservative | preservative |
| Phase B | |
| 8.90 Dehyton ® PK 45 | Cocamidopropyl Betaine |
| 35.70 Texapon ® NSO (9.7% surfactant fraction) | Sodium Laureth Sulfate |
| Phase C | |
| 1.60 Dispersion 1 | |
| q.s. NaOH 20% | Sodium Hydroxide |
| Phase D | |
| 0.50 D-Panthenol ® USP | Panthenol |
| 2.00 Uvinul ® MC 80 | Ethylhexyl Methoxycinnamate |
| 0.30 Perfume oil | Perfume |
| 0.10 Edeta BD | Disodium EDTA |
| Phase E | |
| 0.70 Sodium chloride | Sodium Chloride |

Preparation:

The components of phase A are weighed in and mixed. Phase B is added one after the other to phase A and dissolved. The components of phase C are added to phase A+B, the pH is adjusted to ca. pH 6 and stirred until homogeneous. Phase D is added and dissolved. The viscosity is adjusted using phase E.

Conditioning Shampoo with Salcare® SC 60

| Ingredient | INCI (manufacturer) |
|---|---|
| Phase A | |
| 0.10 Salcare ® SC 60 | Acrylamidepropyltrimonium Chloride, Acrylamide |
| 15.00 Water dist. | Aqua dem. |
| q.s. Preservative | Presevative |
| Phase B | |
| 1.60 Dispersion 1 | |
| 33.30 Water dist. | Aqua dem. |
| q.s. NaOH 20% | Sodium Hydroxide |
| Phase C | |
| 8.90 Dehyton ® PK 45 | Cocamidopropyl Betaine |
| 35.70 Texapon ® NSO (9.7% surfactant fraction) | Sodium Laureth Sulfate |
| Phase D | |
| 0.50 D-Panthenol ® USP | Panthenol |
| 4.00 Dow Corning ® 1664 | Dimethicone, Laureth-4, Laureth-23 |
| 0.30 Perfume oil | Perfume |
| Phase E | |
| 0.50 Sodium chloride | Sodium chloride |

Preparation:

The components of phase A are weighed in and dissolved. Phase B is weighed in and neutralized with NaOH. Phase C is added to phase B and stirred until homogeneous. Then, the dissolved phase A is added to phase B+C and stirred until homogeneous. The pH is adjusted to ca. pH=6. Phase D is added and dissolved. Phase E is used to adjust the viscosity.

Hair Color Formulation—Developer

| Ingredient | INCI (Manufacturer) |
|---|---|
| Phase A | |
| 80.00 Water dist. | Aqua dem. |
| 0.15 Disodium Phosphate | disodium phosphate |
| Phase B | |
| 5.00 Dispersion 1 | |
| Phase C | |
| 12.00 Hydrogen peroxide (50%) | Hydrogen peroxide |
| 1.00 Glycerol (99%) | Glycerol |
| 1.00 Texapon ® NSO (0.27% surfactant fraction) | Sodium Laureth Sulfate |
| Phase D | |
| q.s. Sequestrante HEDP | Etidronic Acid |

Preparation:

The components of phase A are weighed in and dissolved. The components of phases B and C are then added to phase A and stirred. Phase D is used to adjust the pH to 2.5 to 3.

What is claimed is:

1. A process for the preparation of polymers P, the process comprising polymerizing at least one polymer A and at least one polymer B, wherein
    (A) polymer A comprises, in polymerized-in form:
        a1) 30 to 70% by weight of $C_1$-$C_4$-alkyl(meth)acrylate,
        a2) 30 to 70% by weight of (meth)acrylic acid,
        a3) 0.1 to 20% by weight of monomers substituted with a $C_8$-$C_{30}$-radical, and
        a4) 0 to 20% by weight of further monomers different from a1) to a3), provided that the amounts of a1) to a4) add up to 100% by weight; and
    (B) polymer B comprises, in polymerized-in form:
        b1) at least one monomer b1) which carries at least one amide group, and
        b2) optionally further monomers b2) different from b1);
    wherein one of the polymers A or B is prepared in the presence of the other polymer in each case and
    wherein the preparation of polymer A or B is started when in the region of from 10 to 50% by weight if all monomers to be used for the preparation of the other polymer in each case have been polymerized and is ended before more than 80% by weight of the amount of all monomers to be used for the preparation of the other polymer have been polymerized.

2. The process according to claim 1, wherein the preparation of the polymers A and B takes place by radical emulsion polymerization.

3. The process according to claim 1, wherein the polymer P comprises the polymers A and B in a weight ratio A:B in the range from 50:50 to 98:2.

4. The process according to claim 1, wherein at least one monomer b1) is methacrylamide.

5. The process according to claim 1, wherein a1) comprises ethyl acrylate and a2) comprises methacrylic acid.

6. The process according to claim 2, wherein the polymer P comprises the polymers A and B in a weight ratio A:B in the range from 50:50 to 98:2.

* * * * *